US009450536B2

(12) United States Patent
Nakanishi et al.

(10) Patent No.: US 9,450,536 B2
(45) Date of Patent: Sep. 20, 2016

(54) INSPECTION APPARATUS AND INSPECTION METHOD

(71) Applicants: SCREEN Holdings Co., Ltd., Kyoto (JP); OSAKA UNIVERSITY, Osaka (JP)

(72) Inventors: Hidetoshi Nakanishi, Kyoto (JP); Akira Ito, Kyoto (JP); Iwao Kawayama, Osaka (JP); Masayoshi Tonouchi, Osaka (JP)

(73) Assignees: SCREEN HOLDINGS CO., LTD., Kyoto (JP); OSAKA UNIVERSITY, Osaka (JP)

( * ) Notice: Subject to any disclaimer, the term of this patent is extended or adjusted under 35 U.S.C. 154(b) by 0 days.

(21) Appl. No.: 14/620,130

(22) Filed: Feb. 11, 2015

(65) Prior Publication Data

US 2015/0236642 A1    Aug. 20, 2015

(30) Foreign Application Priority Data

Feb. 18, 2014    (JP) ................................ 2014-028573

(51) Int. Cl.

| | |
|---|---|
| G01J 5/02 | (2006.01) |
| H02S 50/15 | (2014.01) |
| G01N 21/95 | (2006.01) |
| G01N 21/3581 | (2014.01) |

(52) U.S. Cl.
CPC .............. *H02S 50/15* (2014.12); *G01N 21/95* (2013.01); *G01N 21/3581* (2013.01); *G01N 2201/0697* (2013.01); *G01N 2201/06113* (2013.01)

(58) Field of Classification Search
CPC ..................... H02S 50/10; G06T 2207/30148; G01N 21/3581
See application file for complete search history.

(56) References Cited

U.S. PATENT DOCUMENTS

| | | |
|---|---|---|
| 6,349,128 B1 * | 2/2002 | Nelson ............................. 378/44 |
| 8,129,683 B2 | 3/2012 | Itsuji et al. |
| 8,872,114 B2 | 10/2014 | Nakanishi et al. |
| 2011/0235046 A1 * | 9/2011 | Maruyama et al. .......... 356/456 |
| 2012/0004868 A1 * | 1/2012 | Fafard ............................. 702/58 |
| 2013/0015368 A1 * | 1/2013 | Nakanishi et al. ........ 250/459.1 |

FOREIGN PATENT DOCUMENTS

| | | |
|---|---|---|
| JP | 2009-175127 A | 8/2009 |
| JP | 2013-019861 A | 1/2013 |

\* cited by examiner

*Primary Examiner* — David Porta
*Assistant Examiner* — Hugh H Maupin
(74) *Attorney, Agent, or Firm* — McDermott Will & Emery LLP

(57) ABSTRACT

An inspection apparatus includes an irradiation part that emits plural pieces of pulse light having different wavelengths to irradiate a multi-junction type solar cell; a wavelength setting part that sets the wavelengths of the plural pieces of pulse light with which the multi-junction type solar cell is irradiated by the irradiation part; and a detection part that detects an electric field intensity of an electromagnetic wave emitted from the multi-junction type solar cell in response to the plural pieces of pulse light with which the multi-junction type solar cell is irradiated by the irradiation part. The irradiation part includes a delay element that delays a time the multi-junction type solar cell is irradiated with the pulse light by a time $\Delta t11$ relative to the pulse light.

7 Claims, 13 Drawing Sheets

F I G. 3
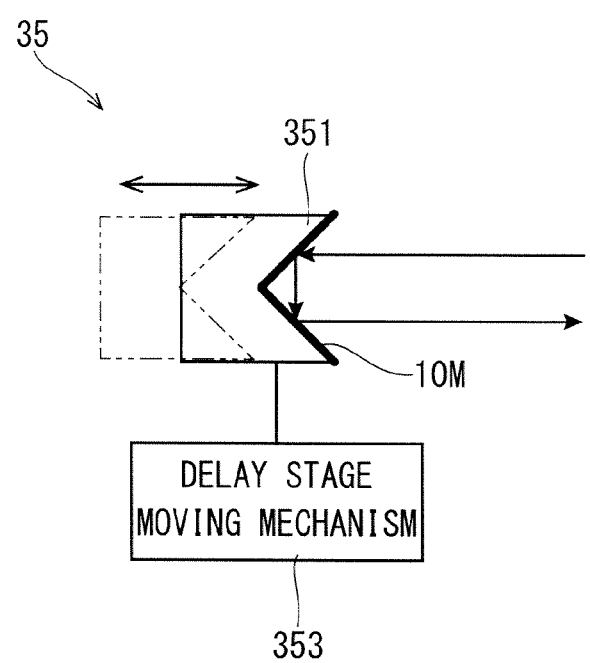

F I G. 6
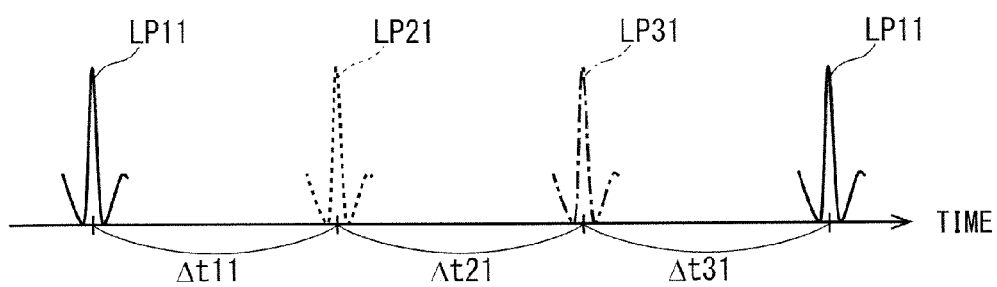
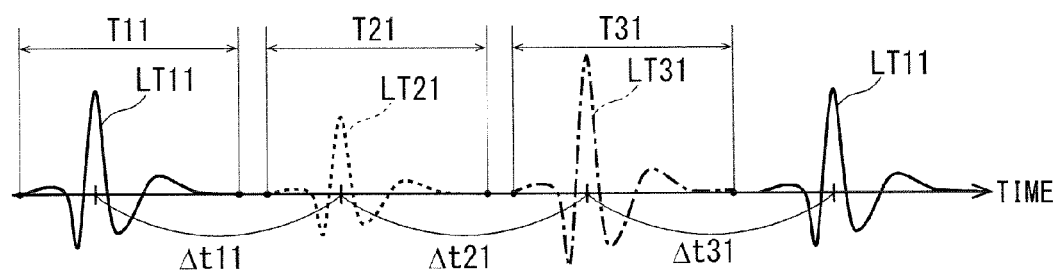

F I G . 1 3
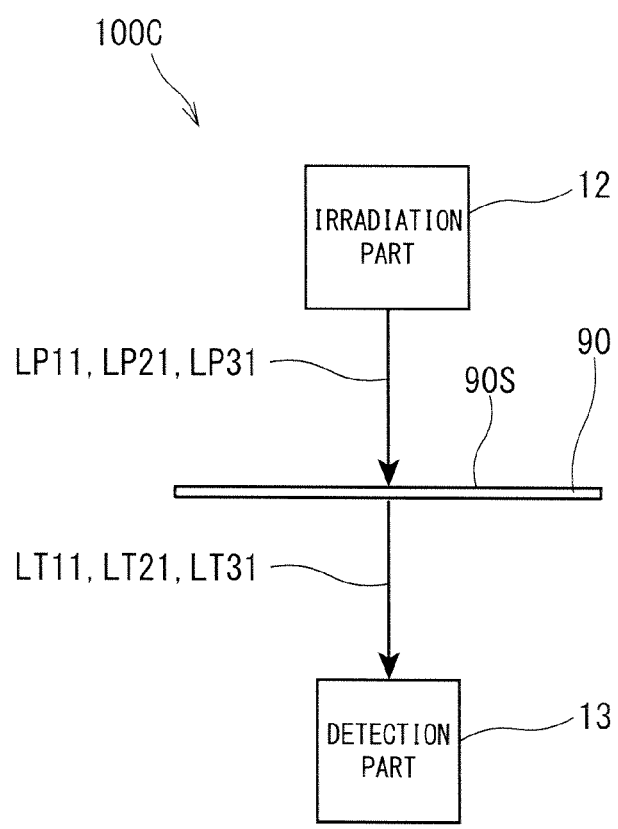

INSPECTION APPARATUS AND INSPECTION METHOD

RELATED APPLICATIONS

This application claims the benefit of Japanese Application No. 2014-028573, filed on Feb. 18, 2014, the disclosure of which Application is incorporated by reference herein.

BACKGROUND OF THE INVENTION

1. Field of the Invention

The present invention relates to a technology of inspecting a photo device.

2. Description of the Background Art

Conventionally, there has been a technology of irradiating a photo device such as a solar cell with light to inspect the photo device based on an electromagnetic wave that is emitted from the photo device in response to the irradiation (for example, see Japanese Patent Application Laid-Open No. 2013-19861).

However, in the case of photo devices, such as a multi-junction type solar cell, which have a portion in which an absorption wavelength region varies in a depth direction, the light reaches a specific depth only by irradiating the photo device with light having a specific wavelength, and only the electromagnetic wave generated at the specific depth can be detected. Therefore, there is a room for improvement in the conventional inspection technology.

SUMMARY OF THE INVENTION

The present invention is aimed at an inspection apparatus that inspects a photo device.

According to one aspect of the present invention, an inspection apparatus includes: an irradiation part that emits plural pieces of light having different wavelengths to irradiate a photo device; a setting part that sets the wavelengths of the plural pieces of light with which the photo device is irradiated by the irradiation part; and a detection part that detects an electric field intensity of an electromagnetic wave emitted from the photo device in response to the plural pieces of light with which the photo device is irradiated by the irradiation part.

Each portion in the depth direction of the photo device can be irradiated with the light having the wavelength corresponding to the absorption wavelength region of the portion. Therefore, the electromagnetic wave can properly be emitted from each portion in the depth direction. Accordingly, each portion in the depth direction of the photo device can well be inspected.

Preferably the irradiation part irradiates the photo device with light having a second wavelength different from a first wavelength after a time $\Delta t$ elapses since the photo device is irradiated with light having the first wavelength.

Because the photo device is irradiated with the pieces of light having the two different wavelengths while the pieces of light are shifted from each other by the time $\Delta t$, the emitted electromagnetic waves can be detected while shifted from each other by the time $\Delta t$.

Preferably the inspection apparatus further includes a delay part that delays a time a detector detects the electromagnetic wave relative to a time the detector receives pulse light. At this point, the plural pieces of light having the different wavelengths emitted from the irradiation part are the pulse light, and the detection part includes the detector that detects the electromagnetic wave by receiving the pulse light emitted from the irradiation part.

Data used to restore the electromagnetic wave can be collected. The electric field intensities of the electromagnetic waves emitted by the plural pieces of pulse light having the different wavelengths can simultaneously be acquired. Therefore, the inspection can efficiently be performed.

Preferably the inspection apparatus further includes: a scanning mechanism that scans the photo device with the plural pieces of light with which the photo device is irradiated by the irradiation part; and an image generation part that generates an image indicating an electric field intensity distribution in the photo device based on the electric field intensity of the electromagnetic wave detected by the detection part.

The inspection can be performed based on the electric field intensity distribution of the electromagnetic wave.

Preferably the plural pieces of light having the different wavelengths emitted from the irradiation part are the pulse light, and the time $\Delta t$ is longer than a generation time for one pulse of the electromagnetic wave emitted by the pulse light.

The electromagnetic waves generated by the plural pieces of pulse light having the different wavelengths can separately be detected.

Preferably the photo device is constructed by stacking materials having different absorption wavelength regions.

The portion existing in the target depth can properly be inspected in the photo device that is formed by stacking the materials having the different absorption wavelength regions.

Preferably the photo device includes a first layer and a second layer having an absorption wavelength region different from that of the first layer, the second layer being provided below the first layer, and the plural pieces of light having the different wavelengths includes first light having energy higher than an energy gap of the first layer and second light having energy that is higher than an energy gap of the second layer and is lower than the energy gap of the first layer.

The electromagnetic wave can well be emitted from each of the first and second layers.

Preferably the photo device is a multi-junction type solar cell.

In the multi-junction type solar cell, a specific solar cell can be inspected by emitting the electromagnetic wave from the specific solar cell in the unitary stacked solar cell.

The present invention is also aimed at an inspection method for inspecting the photo device.

According to another aspect of the present invention, an inspection method includes the steps of: emitting plural pieces of light having different wavelengths to irradiate a photo device; setting the wavelengths of the plural pieces of light with which the photo device is irradiated in the irradiation step; and detecting an electromagnetic wave emitted from the photo device in response to the plural pieces of light with which the photo device is irradiated in the irradiation step.

Each portion in the depth direction of the photo device can be irradiated with the light having the wavelength corresponding to the absorption wavelength region of the portion. Therefore, the electromagnetic wave can properly be emitted from each portion in the depth direction. Accordingly, each portion in the depth direction of the photo device can well be inspected.

Preferably the irradiation step includes the step of irradiating the photo device with light having a second wavelength different from a first wavelength after a time Δt elapses since the photo device is irradiated with the light having the first wavelength.

Because the photo device is irradiated with the pieces of light having the two wavelengths while the pieces of light are shifted from each other by the time Δt, the emitted electromagnetic waves can be detected while being shifted from each other by the time Δt.

Therefore, an object of the present invention is to provide a technology of properly inspecting each portion in the depth direction of the photo device.

These and other objects, features, aspects and advantages of the present invention will become more apparent from the following detailed description of the present invention when taken in conjunction with the accompanying drawings.

BRIEF DESCRIPTION OF THE DRAWING

FIG. 3 is a schematic diagram illustrating configurations of a delay element;

FIG. 6 is a conceptual view illustrating a pulse string of pieces of pulse light with which the multi-junction type solar cell is irradiated (upper part) and a pulse string of electromagnetic waves emitted from the multi-junction type solar cell (lower part);

FIG. 13 is a schematic diagram illustrating an inspection apparatus according to a fourth preferred embodiment.

DESCRIPTION OF THE PREFERRED EMBODIMENTS

Figure 1:
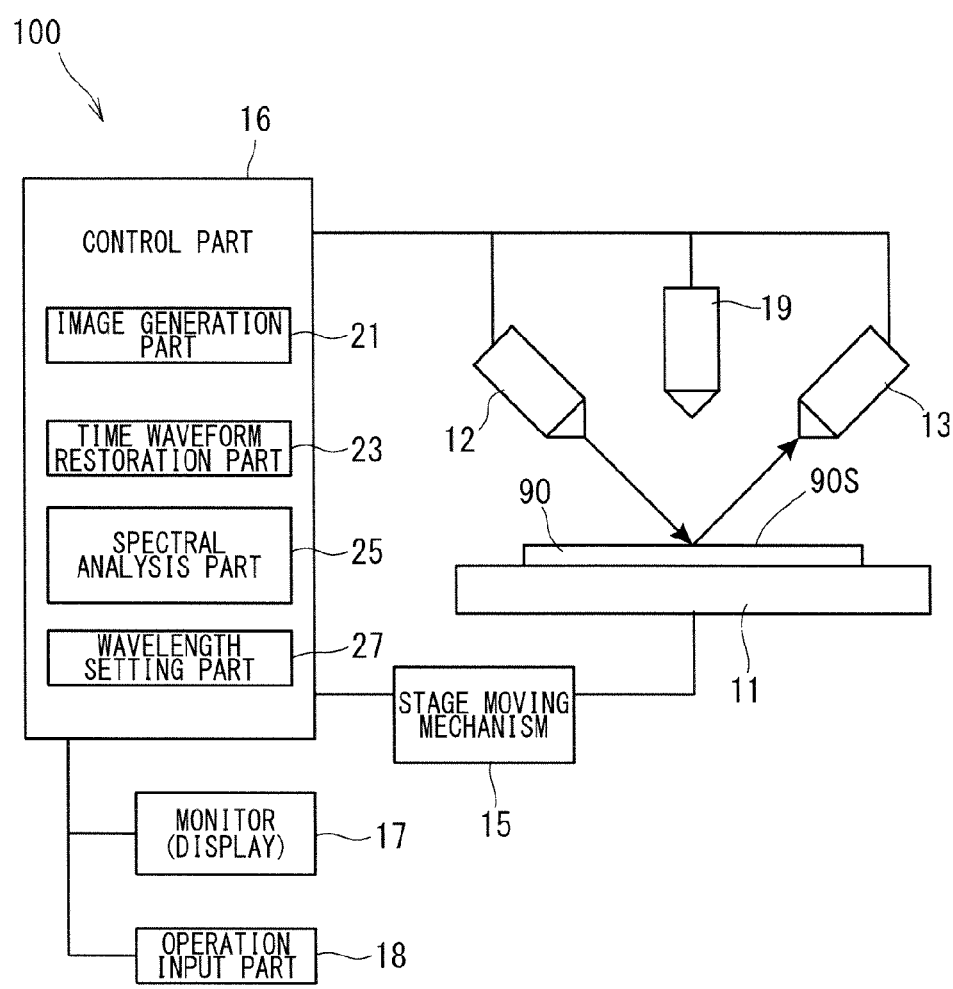
FIG. 1 is a schematic diagram illustrating a configuration of an inspection apparatus according to a first preferred embodiment.

Hereinafter, preferred embodiments of the present invention will be described below with reference to the accompanying drawings. In the drawings, for the sake of easy understanding, a size of each part or the number of parts is exaggerated or simplified as needed basis.

1. First Preferred Embodiment 1.1. Configuration and Function

Figure 2:
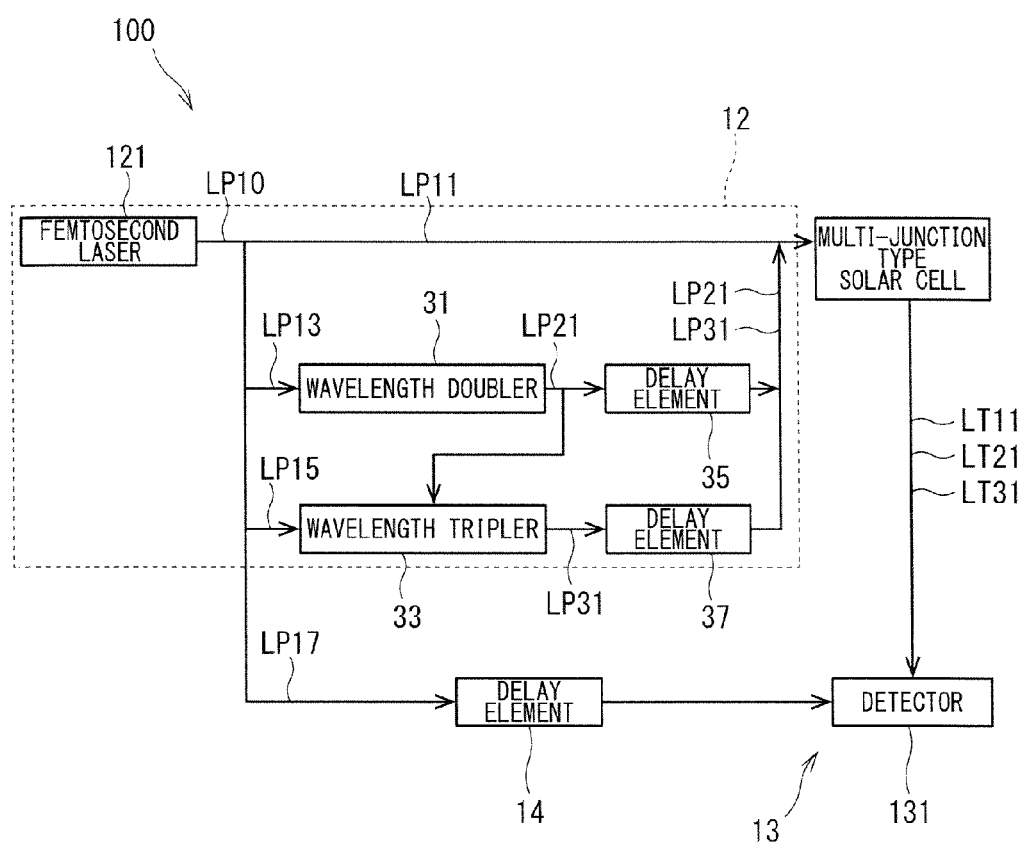
FIG. 2 is a schematic diagram illustrating configurations of an irradiation part and a detection part that are included in the inspection apparatus.

FIG. 1 is a schematic diagram illustrating a configuration of an inspection apparatus 100 according to a first preferred embodiment. FIG. 2 is a schematic diagram illustrating configurations of an irradiation part 12 and a detection part 13 that are included in the inspection apparatus 100.

The inspection apparatus 100 irradiates an inspection object that is of a photo device with pulse light, and detects an electromagnetic wave (for example, a terahertz wave having frequencies of 0.1 THz to 30 THz) that is emitted from the inspection object in response to the irradiation of the inspection object with the pulse light, thereby inspecting the inspection object.

As used herein, the photo device means electronic devices, such as a photodiode, image sensors such as a CMOS sensor and a CCD sensor, a solar cell, and an LED, in which a semiconductor photoelectric effect is used. The surface of the inspection object is formed flat. Alternatively, the surface of the inspection object may be formed into a curved shape. In the first preferred embodiment, the case that a multi-junction type solar cell 90 is inspected as the inspection object will be described. However, other photo devices can similarly be inspected.

As illustrated in FIGS. 1 and 2, the inspection apparatus 100 includes a stage 11, the irradiation part 12, the detection part 13, a delay element 14, a stage moving mechanism 15, a control part 16, a monitor 17, a operation input part 18, and a camera 19.

The multi-junction type solar cell 90 is held on the stage 11 by fixing means (not shown). Examples of the fixing means include means in which a clipping tool clipping a substrate is used, an adhesive sheet, and a suction hole formed in a surface of the stage 11. Alternatively, any fixing means may be used as long as the multi-junction type solar cell 90 can be fixed. In the first preferred embodiment, the multi-junction type solar cell 90 is held on the stage 11 such that the irradiation part 12 and the detection part 13 are arranged on a side of a light receiving surface (surface 90S) of the multi-junction type solar cell 90. Therefore, the inspection apparatus 100 is a reflection type inspection apparatus that detects the electromagnetic wave emitted on the side identical to that of an irradiated surface.

As illustrated in FIG. 2, the irradiation part 12 includes a femtosecond laser 121. For example, the femtosecond laser 121 emits pulse light (pulse light LP10) having a wavelength including visible light regions of 360 nm (nanometer) to 1.5 μm (micrometer). Specifically, the femtosecond laser 121 emits the linearly-polarized pulse light having a center wavelength of around 800 nm, periods of several kilohertz to several hundred megahertz, and pulse widths of about 10 femtosecond to about 150 femtosecond.

The pulse light LP10 emitted from the femtosecond laser 121 is split into pieces of pulse light LP11, LP13, LP15, and LP17 by a beam splitter or the like. The pulse light LP11 is guided to the multi-junction type solar cell 90. The pulse light LP13 is guided to a wavelength doubler 31. The pulse light LP15 is guided to a wavelength tripler 33. The pulse light LP17 is guided to a detector 131 of the detection part 13 detecting the electromagnetic wave through the delay element 14.

The wavelength doubler 31 is a second harmonic generation device made of a non-linear optical crystal. Specifically, for example, the wavelength doubler 31 is made of a beta barium borate (BBO) crystal, a potassium titanyl arsenate (KTA) crystal, or a potassium dihydrogen phosphate (KDP) crystal, and generates pulse light LP21 having a wavelength $\lambda/2$ from the pulse light LP13 having a wavelength $\lambda$. The generated pulse light LP21 is split into two, one of the pieces of pulse light LP21 is guided to a delay element 35, and the other piece of pulse light LP21 is guided to the wavelength tripler 33. The pulse light LP21 passing through the delay element 35 is guided to the multi-junction type solar cell 90.

FIG. 3 is a schematic diagram illustrating a configuration of the delay element 35. The delay element 35 includes a delay stage 351 and a delay stage moving mechanism 353. The delay stage 351 includes a mirror 10M that reflects the pulse light LP21 toward an incident direction. The delay stage moving mechanism 353 moves the mirror 10M along the incident direction of the pulse light LP21.

The delay stage moving mechanism 353 is controlled by the control part 16. The delay element 35 moves the delay stage 351 to continuously change an optical path length of the pulse light LP21. When the optical path length of the pulse light LP21 is changed, a phase of the pulse light LP21 reaching the multi-junction type solar cell 90 is shifted relative to a phase of the pulse light LP11 reaching the multi-junction type solar cell 90. Therefore, a time the pulse light LP21 reaching the multi-junction type solar cell 90 can be delayed relative to a time the pulse light LP11 reaches the multi-junction type solar cell 90. In the following description, sometimes the delayed time is also written as Δt.

The delay element 35 may have the configuration different from the delay stage 351. Specifically, an electro-optical effect may be used. That is, an electro-optical element in which a refractive index is changed by changing an applied voltage may be used as the delay element 35. For example, the electro-optical element disclosed in Japanese Patent Application Laid-Open No. 2009-175127 may be used.

The wavelength tripler 33 is a third harmonic generation device made of a non-linear optical crystal. Specifically, for example, the wavelength tripler 33 is made of a cesium lithium borate (CLBO) crystal, for example, and generates pulse light LP31 having a wavelength $\lambda/3$ by a sum frequency generation technology of synthesizing the pulse light LP15 and the pulse light LP21. The generated pulse light LP31 is guided to a delay element 37. The pulse light LP31 passing through the delay element 37 is guided to the multi-junction type solar cell 90.

The delay element 37 has a configuration substantially similar to that of the delay element 35 shown in FIG. 3. The delay element 37 delays the time the pulse light LP31 reaches the multi-junction type solar cell 90 relative to the time the pieces of pulse light LP and LP21 reach the multi-junction type solar cell 90.

In the first preferred embodiment, the optical path lengths of the pieces of pulse light LP21 and LP31 are changed by the delay elements 35 and 37. Alternatively, for example, the optical path lengths of the pieces of pulse light LP11 and LP21 or the pieces of pulse light LP11 and LP31 may be changed. That is, the times the pieces of pulse light LP11, LP21, and LP31 reach the multi-junction type solar cell 90 may relatively be shifted from one another.

The pieces of pulse light LP11, LP21, and LP31 guided to the multi-junction type solar cell 90 is modulated at several kilohertz by a light chopper (not illustrated). For example, an AOM (Acousto-Optic Modulator) can be used as a modulation element. The multi-junction type solar cell 90 is irradiated with the modulated pieces of pulse light LP11, LP21, and LP31.

As illustrated in FIG. 1, the irradiation part 12 irradiates the multi-junction type solar cell 90 with the pieces of pulse light LP11, LP21, and LP31 from the side of the surface 90S that is of the light receiving surface of the multi-junction type solar cell 90. The irradiation part 12 irradiates the multi-junction type solar cell 90 with the pieces of pulse light LP11, LP21, and LP31 such that an optical axis of the pulse light LP11 is obliquely incident to the light receiving surface of the multi-junction type solar cell 90. In the first preferred embodiment, an irradiation angle is set such that an incident angle becomes 45 degrees. However, the incident angle is not limited to 45 degrees, but the incident angle can be properly changed within a range of 0 degree to 90 degrees.

Figure 4:
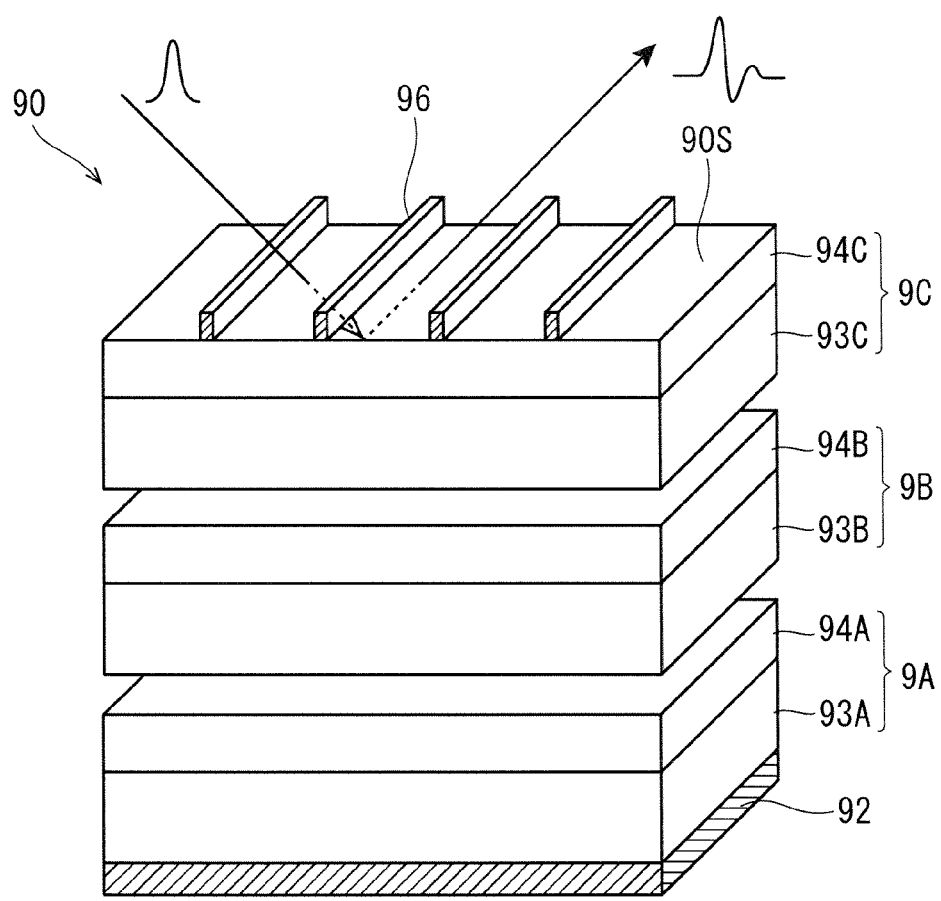
FIG. 4 is a schematic sectional view of a multi-junction type solar cell.

FIG. 4 is a schematic sectional view of the multi-junction type solar cell 90. The multi-junction type solar cell 90 is constructed by stacking materials having different absorption wavelength regions in the depth direction. More particularly, the multi-junction type solar cell 90 is constructed by stacking three unitary solar cells 9A, 9B, and 9C having the absorption wavelength regions different from one another in the ascending order. The solar cells 9A and 9B are electrically connected to each other, and the solar cells 9B and 9C are electrically connected to each other.

As used herein, the absorption wavelength region means a wavelength region that is mainly absorbed by each of the unitary solar cells 9A, 9B, and 9C, and can also be called a use wavelength region. The plural solar cells 9A, 9B, and 9C may not completely differ from one another in the absorption wavelength region, but the absorption wavelength regions of the solar cells 9A, 9B, and 9C may partially overlap one another.

In the solar cells 9A, 9B, and 9C, p-type semiconductor layers 93A, 93B, and 93C are joined to n-type semiconductor layers 94A, 94B, and 94C to form pn-junctions, respectively. A plate-shape backside electrode 92 made of aluminum or the like is attached to a lower surface of the solar cells 9A constituting the back side of the multi-junction type solar cell 90.

A light receiving surface electrode 96 made of aluminum or the like is attached to an upper surface of the solar cells 9C constituting the light receiving surface (surface 90S) of the multi-junction type solar cell 90. For example, the light receiving surface electrode 96 is formed into a comb shape or a lattice shape such that the light passes easily therethrough. The light receiving surface electrode 96 may be constructed with a transparent electrode.

In principal surfaces on both sides of the multi-junction type solar cell 90, the principal surface on the side on which the light receiving surface electrode 96 is provided constitutes the light receiving surface. That is, the multi-junction type solar cell 90 is designed to suitably generate power by receiving the light from the light receiving surface side.

When a region where an internal electric field of the multi-junction type solar cell 90 exists is irradiated with the pulse light LP11 having energy exceeding a bandgap, photocarriers (free electrons and holes) are generated, and accelerated by the internal electric field. In the accelerated photocarriers, the holes move to the backside electrode 92, and the free electrons move to the light receiving surface electrode 96. Therefore, a pulse-shape current is generated, and a pulse-shape electromagnetic wave is generated according to the pulse-shape current. It is well known that the internal electric field is generated in the pn-junction or a Schottky junction.

In the inspection apparatus 100 of the first preferred embodiment, the multi-junction type solar cell 90 can be irradiated with the pieces of pulse light LP11, LP21 and LP31 having three wavelengths different from one another. Therefore, the multi-junction type solar cell 90 is irradiated with the pieces of pulse light LP11, LP21, and LP31, electromagnetic waves LT11, LT21, and LT31 are emitted according to the pieces of pulse light LP11, LP21, and LP31.

The electromagnetic waves LT11, LT21, and LT31 emitted from the multi-junction type solar cell 90 are guided to the detector 131 included in the detection part 13. The detector 131 is constructed with a photoconductive switch (photoconductive antenna) to which the pulse light LP11 is incident. For example, a dipole type photoconductive switch, a bow-tie type photoconductive switch, and a spiral type photoconductive switch are well known. When the detector 131 is irradiated with the pulse light LP11 while the electromagnetic wave LT11, LT21, or LT31 is incident to the detector 131, the current is instantaneously generated in the photoconductive switch according to an electric field intensity of the electromagnetic wave LT11, LT21, or LT31. The current corresponding to the electric field intensity is converted into a digital quantity through a lock-in amplifier, an I/V conversion circuit, and an A/D conversion circuit (all of which are not illustrated). Thus, the detection part 13 detects the electric field intensities of the electromagnetic waves LT11, LT21, and LT31 emitted from the multi-junction type solar cell 90 in response to the irradiation of the multi-junction type solar cell 90 with the pulse light LP17.

Other elements such as a Schottky barrier diode may be used as the detector 131. The Schottky barrier diode has a characteristic having small polarization dependence. Alternatively, a non-linear optical crystal may be used as the detector 131.

The delay element 14 (delay part) is provided on an optical path of the pulse light LP17 to the detector 131. The delay element 14 changes the time the pulse light LP17 reaches the detector 131 by changing the optical path length of the pulse light LP17. A basic configuration of the delay element 14 is similar to that of the delay element 35 shown in FIG. 3.

The delay element 14 shifts the phase of the pulse light LP17 reaching the detector 131 relative to the phases of the electromagnetic waves LT11, LT21, and LT31 reaching the detector 131. That is, the time the pulse light LP17 reaches the detector 131 is delayed relative to the time the electromagnetic waves LT11, LT21, and LT31 reach the detector 131. The delay element 14 changes the optical path length of the pulse light LP17, which allows the detector 131 to delay the times (detection times or sampling times) the electric field intensities of the electromagnetic waves LT11, LT21, and LT31 are detected.

Alternatively, not the optical path length of the pulse light LP17, but the optical path lengths of the pieces of pulse light LP11, LP21, and LP31 or the optical path lengths of the electromagnetic waves LT11, LT21, and LT31 emitted from the multi-junction type solar cell 90 may be changed. Even in this case, the time the electromagnetic waves LT11, LT21, and LT31 reach the detector 131 can be shifted relative to the time the pulse light LP17 reaches the detector 131. That is, the time the detector 131 detects the electric field intensities of the electromagnetic waves LT11, LT21, and LT31 can be delayed. Therefore, the electric field intensities of the electromagnetic waves LT11, LT21, and LT31 can be detected in different phase, respectively Although not illustrated, a reverse bias voltage may be applied to the multi-junction type solar cell 90 during the inspection. Specifically, a voltage applying circuit is connected to the light receiving surface electrode 96 and backside electrode 92 of the multi-junction type solar cell 90 to apply the reverse bias voltage. The reverse bias voltage applied to the multi-junction type solar cell 90 by the voltage applying circuit may be varied under the control of the control part 16.

The depletion layer of the pn-junction in the multi-junction type solar cell 90 can be enlarged by applying the reverse bias voltage. Therefore, the electric field intensities of the electromagnetic waves LT11, LT21, and LT31 detected by the detector 131 can be enhanced.

The electric field intensities of the electromagnetic waves LT11, LT21, and LT31 can be enhanced by not applying the reverse bias voltage, but short-circuiting between the light receiving surface electrode 96 and the backside electrode 92.

The configuration of the inspection apparatus 100 will further be described. The stage moving mechanism 15 is a device that moves the stage 11 in a two-dimensional plane. For example, the stage moving mechanism 15 is constructed with an X-Y table or the like. The stage moving mechanism 15 moves the multi-junction type solar cell 90 held by the stage 11 relative to the irradiation part 12. In the inspection apparatus 100, the stage moving mechanism 15 can move the multi-junction type solar cell 90 to any position in the two-dimensional plane.

In the first preferred embodiment, the stage moving mechanism 15 moves the stage 11 in the X-Y direction, which allows a required inspection range on the multi-junction type solar cell 90 to be scanned with the pieces of pulse light LP11, LP21, and LP31. That is, the stage moving mechanism 15 constitutes the scanning mechanism.

Alternatively, the scanning of the inspection range may be performed by changing the optical paths of the pieces of pulse light LP11, LP21, and LP31 instead of moving the stage 11 with the stage moving mechanism 15. Specifically, a galvano-mirror (not illustrated) is provided, and the surface 90S of the multi-junction type solar cell 90 is scanned with the pulse light LP11 in two directions that are parallel to the surface 91S and orthogonal to each other. A polygon mirror, a piezoelectric mirror, or an acousto-optical element is considered to be used instead of the galvano-mirror.

The control part 16 is constructed with a general computer including a CPU, a ROM, and a RAM (all of which are not illustrated). The control part 16 is connected to the femtosecond laser 121, the detector 131, the delay elements 35 and 37, the delay element 14, and the stage moving mechanism 15 or the like. The control part 16 controls operations of these units, and receives data from these units.

The control part 16 includes an image generation part 21, a time waveform restoration part 23, a spectral analysis part 25, and a wavelength setting part 27 shown in FIG. 1. The image generation part 21, the time waveform restoration part 23, the spectral analysis part 25, and the wavelength setting part 27 may be implemented as a function by the operation of the CPU included in the control part 16 according to a program, or implemented in a hardware manner by a dedicated circuit.

The image generation part 21 generates an electric field intensity distribution image in which an electric field intensity distribution of the electromagnetic wave emitted by the irradiation of the inspection object range (a part or a whole of the multi-junction type solar cell 90) of the multi-junction type solar cell 90 with the pieces of pulse light LP11, LP21, and LP31 is visualized. In the electric field intensity distribution image, a difference in electric field intensity is visually expressed by a different color, shading, or a different pattern.

The time waveform restoration part 23 restores a time waveform of the electromagnetic wave emitted from the multi-junction type solar cell 90 based on the electric field intensity detected by the detector 131. Specifically, the time the pulse light LP17 reaches the detector 131 is changed by driving the delay element 14, thereby acquiring the electric field intensity of the electromagnetic wave detected in each phase. The time waveform of the electromagnetic wave is restored by plotting the acquired electric field intensity on a time axis.

The spectral analysis part 25 performs a spectral analysis of the multi-junction type solar cell 90 based on the restored time waveform of the electromagnetic wave Particularly, the spectral analysis part 25 acquires an amplitude intensity spectrum concerning the frequency by performing a Fourier transform of time waveform information.

The wavelength setting part 27 sets the wavelength of the pulse light with which the irradiation part 12 irradiates the multi-junction type solar cell 90. More specifically, in the pieces of pulse light LP11, LP21, and LP31 having the wavelengths different from one another, the wavelength setting part 27 sets the pulse light with which the multi-junction type solar cell 90 is irradiated based on input information through the operation input part 18 described later. The irradiation part 12 irradiates the multi-junction type solar cell 90 with the pulse light having the wavelength set by the wavelength setting part 27. For example, in the pieces of pulse light LP11, LP21, and LP31, the pieces of pulse light that are not used in the irradiation by the setting of the wavelength setting part 27 are blocked by a shielding plate thereby the irradiation is suppressed.

In the case that the femtosecond laser 121 is a variable wavelength laser, the wavelength of the pulse light LP10 emitted from the femtosecond laser 121 may be set by the wavelength setting part 27.

The monitor 17 and the operation input part 18 are connected to the control part 16. The monitor 17 is a display device such as a liquid crystal display, and displays various pieces of image information to the operator. For example, the image of the surface 90S of the multi-junction type solar cell 90 photographed by the camera 19, the electric field intensity distribution image generated by the image generation part 21, the time waveforms of the electromagnetic waves LT11, LT21, and LT31 restored by the time waveform restoration part 23, and the spectral information acquired by the spectral analysis part 25 are displayed on the monitor 17. A GUI (Graphical User Interface) screen necessary to set an inspection condition (inspection range or the like) may be displayed on the monitor 17.

The operation input part 18 is constructed with various input devices such as a mouse and a keyboard. The operator can perform a predetermined manipulation input through the operation input part 18. When a touch panel is used as the monitor 17, the monitor 17 may also act as the operation input part 18.

The control part 16 is connected to a storage in which various pieces of data are stored. The storage is constructed with a portable medium (such as a magnetic medium, an optical disk medium, and a semiconductor memory) in addition to a fixed disk such as a hard disk. The control part 16 and the storage may be connected to each other through a network.

1.2 Inspection

<1.2.1. Inspection Example 1>

Figure 5:
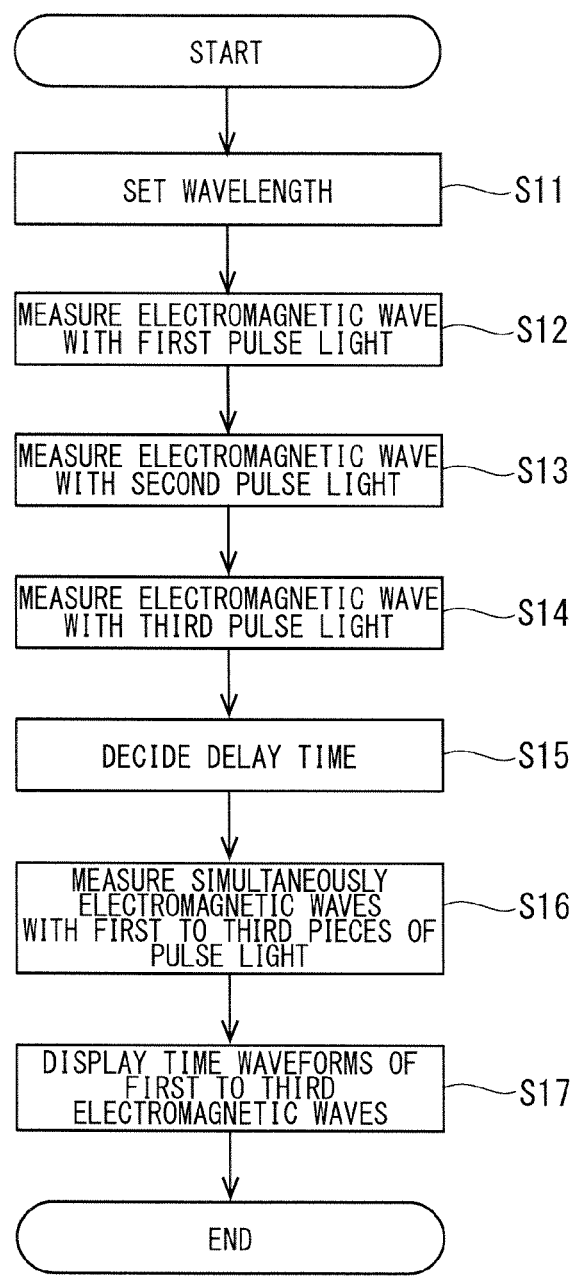
FIG. 5 is a view illustrating a flow of an inspection example 1.

FIG. 5 is a view illustrating a flow of an inspection example 1. In the inspection example 1, the characteristic or the like of the multi-junction type solar cell 90 is evaluated at a specific position by restoring the electromagnetic wave generated at the specific position (inspection object place) in the multi-junction type solar cell 90. Hereinafter, unless otherwise noted, it is assumed that the inspection apparatus 100 performs each operation under the control of the control part 16.

In the inspection example 1, the wavelength of the pulse light used in the irradiation is set based on an absorption wavelength region of each layer of the multi-junction type solar cell 90 (Step S11, the setting process). At this point, it is assumed that the pieces of pulse light LP11, LP21, and LP31 having three wavelengths $\lambda$, $\lambda/2$, and $\lambda/3$ are set such that the multi-junction type solar cell 90 is irradiated with the pieces of pulse light LP11, LP21, and LP31.

The inspection apparatus 100 irradiates the multi-junction type solar cell 90 only with the pulse light LP11 (first pulse light) to measure the emitted electromagnetic wave LT11 (first electromagnetic wave) (Step S12). The inspection apparatus 100 irradiates the multi-junction type solar cell 90 only with the pulse light LP21 (second pulse light) to measure the emitted electromagnetic wave LT21 (second electromagnetic wave) (Step S13). The inspection apparatus 100 irradiates the multi-junction type solar cell 90 only with the pulse light LP31 (third pulse light) to measure the emitted electromagnetic wave LT31 (third electromagnetic wave) (Step S14).

In Steps S12 to Step S14, the time (phase) the electric field intensity of the electromagnetic wave is changed by one time of the delay stage of the delay element 14 scan, thereby acquiring data used to restore the time waveform of the electromagnetic wave. There is no particular limitation to the measurement position of the electromagnetic wave in the multi-junction type solar cell 90. However, desirably the measurement position is a place, such as a neighborhood of the light receiving surface electrode 96, where the electromagnetic wave is relatively easily generated.

Then, a time Δt the pieces of pulse light LP11, LP21, and LP31 are shifted from one another is determined (Step S15). Specifically, a generation time for one pulse of each of the electromagnetic waves LT11, LT21, and LT31 is acquired based on the time waveforms of the electromagnetic waves LT11, LT21, and LT31 measured in Steps S12 to Step S14. The generation time of the electromagnetic wave means a time period from a change in electric field intensity is started until the change in electric field intensity is completed. A time Δt is decided based on the generation time.

FIG. 6 is a conceptual view illustrating a pulse string of pieces of pulse light with which the multi-junction type solar cell 90 is irradiated (upper part) and a pulse string of electromagnetic waves emitted from the multi-junction type solar cell 90 (lower part). In FIG. 6, two horizontal axes indicate the time axes.

In the inspection example 1, as illustrated in FIG. 6, the multi-junction type solar cell 90 is irradiated with the pulse light LP11 for one pulse, and the multi-junction type solar cell 90 is irradiated with the pulse light LP21 for one pulse after a delay of a time Δt11. Then, the multi-junction type solar cell 90 is irradiated with the pulse light LP31 for one pulse after a delay of a time Δt21. Then, the multi-junction type solar cell 90 is irradiated with the pulse light LP11 for one pulse again after a delay of a time Δt31. This irradiation cycle is repeatedly performed. Therefore, in the multi-junction type solar cell 90, the electromagnetic wave LT11 is generated, the electromagnetic wave LT21 is emitted after the delay of the time Δt11, the electromagnetic wave LT31 is generated after the delay of the time Δt21, and the electromagnetic wave LT11 is generated again after the delay of the time Δt31.

At this point, when the time Δt11 is increased longer than a generation time T11 of the electromagnetic wave LT11, the detector 131 can be constrained from simultaneously detecting electric field intensity components of the electromagnetic waves LT11 and LT21. Accordingly, the electric field intensities of the electromagnetic waves LT11 and LT21 can separately be detected. Similarly, when the time Δt21 is increased longer than a generation time T21 of the electromagnetic wave LT21, the detector 131 can separately detect the electric field intensities of the electromagnetic waves LT21 and LT31. Similarly, when the time Δt31 is increased longer than a generation time T31 of the electromagnetic wave LT31, the detector 131 can separately detect the electric field intensities of the electromagnetic waves LT31 and LT11.

The times Δt11, Δt21, and Δt31 may be equal to one another, or be different from one another. Because the generation times T11, T21, and T31 of the electromagnetic waves LT11, LT21, and LT31 are considered to be different from one another, the times Δt11, Δt21, and Δt31 may properly be decided according to the generation times T11, T21, and T31.

Referring to FIG. 5, when the times Δt1, Δt21, and Δt31 are decided, the previously-set inspection object place in the multi-junction type solar cell 90 is irradiated with the pieces of pulse light LP11, LP21, and LP31 while the pieces of pulse light LP11, LP21, and LP31 are delayed from one another, and the electromagnetic waves LT11, LT21, and LT31 are simultaneously measured (Step S16, the irradiation process and the detection process).

Specifically, a unitary measurement in which the inspection object place is irradiated with the pieces of pulse light LP11, LP21, and LP31 to acquire the electric field intensities of the electromagnetic waves LT11, LT21, and LT31 is repeatedly performed at one time of the delay stage of the delay element 14 scan. Therefore, all the pieces of data used to restore the time waveforms of the electromagnetic waves LT11, LT21, and LT31 are collected.

In the case that the plural inspection object places are set in Step S15, the electric field intensities of the inspection object places are acquired.

When the acquisition of the electric field intensity is completed, the time waveform restored by the time waveform restoration part 23 is displayed on the monitor 17 (Step S17).

Figure 7:
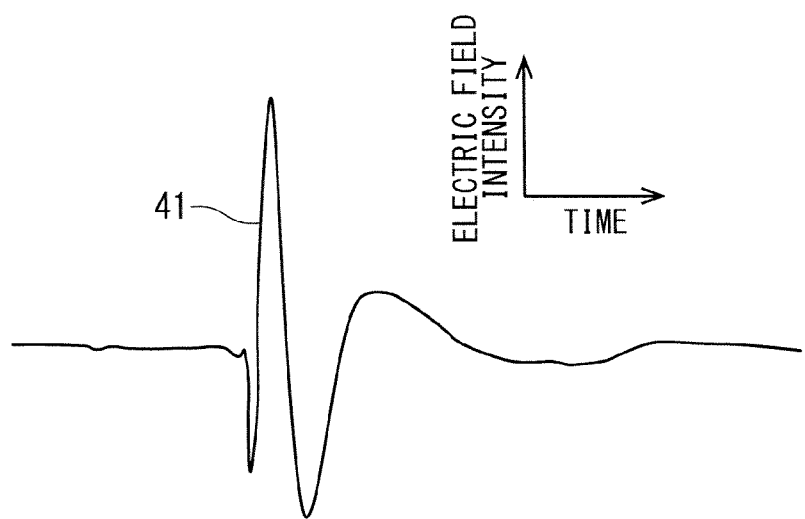
FIG. 7 is a view illustrating a time waveform of the restored electromagnetic wave.

FIG. 7 is a view illustrating a time waveform 41 of the restored electromagnetic wave LT11. As illustrated in FIG. 7, the time waveform 41 of the electromagnetic wave LT11 is restored with respect to the inspection object place by performing Step S16. At the same time, the time waveform of the electromagnetic waves LT21 and LT31 are similarly restored.

It is conceivable that the inspection object place is individually irradiated with the pieces of pulse light LP11, LP21, and LP31 to sequentially acquire all the pieces of data used to restore the time waveform of the electromagnetic wave LT11, all the pieces of data used to restore the time waveform of the electromagnetic wave LT21, and all the pieces of data used to restore the time waveform of the electromagnetic wave LT31. However, in this case, it is necessary to operate the delay stage of the delay element 14 a total of three times for scan. When the number of manipulation times of the delay stage increases, there is a risk of lengthening the inspection time or generating an error in the movement of the delay stage. On the other hand, in the first preferred embodiment, because only one time operation of delay stage for scan, the pieces of data of the electric field intensities of the plural electromagnetic waves LT11, LT21, and LT31 can stably and accurately be acquired at the same time. Additionally, the inspection can efficiently be performed.

During the measurement of the electromagnetic wave in Steps S12 to Step S14 and Step S16, the emitted electromagnetic wave may be enhanced by applying the reverse bias voltage to the multi-junction type solar cell 90.

Figure 8:
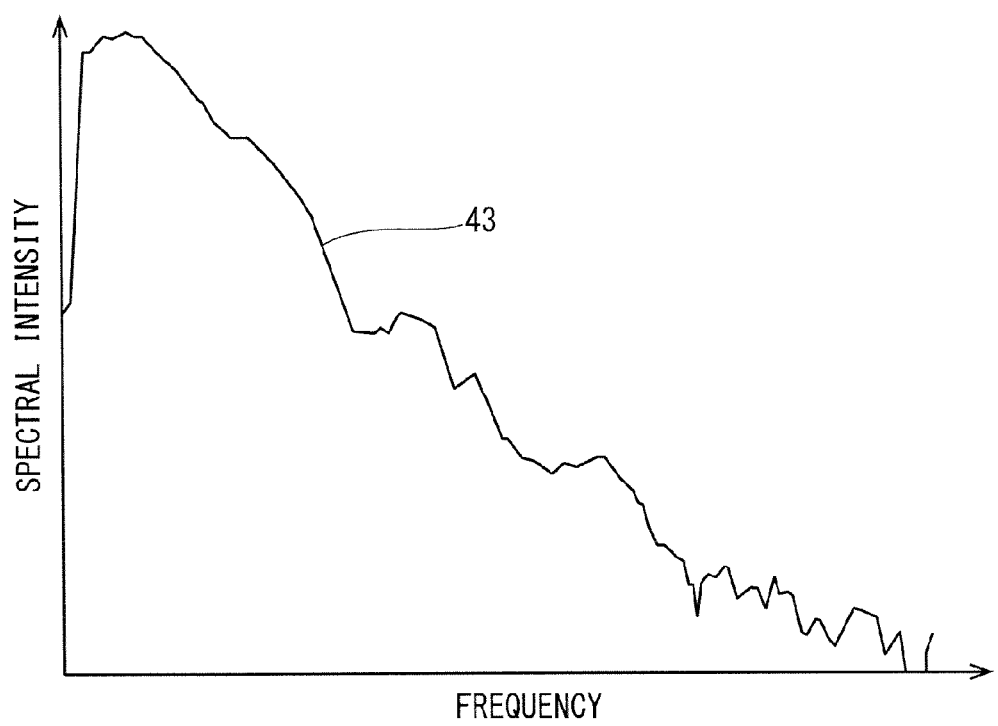
FIG. 8 is a view illustrating an example of a spectral distribution of the electromagnetic wave.

FIG. 8 is a view illustrating an example of a spectral distribution 43 of the electromagnetic wave LT11. In FIG. 8, the vertical axis indicates a spectral intensity and the horizontal axis indicates the frequency. The spectral analysis part 25 performs a Fourier transform to convert a time region into a frequency space, which allows the spectral distribution 43 in FIG. 8 to be acquired from the time waveform 41 shown in FIG. 7. Information on a physical property in the inspection object place can more particularly be analyzed by acquiring the spectral distribution 43. The spectrum analysis may be performed after Step S16 or Step S17.

<1.2.2. Inspection Example 2>

Figure 9:
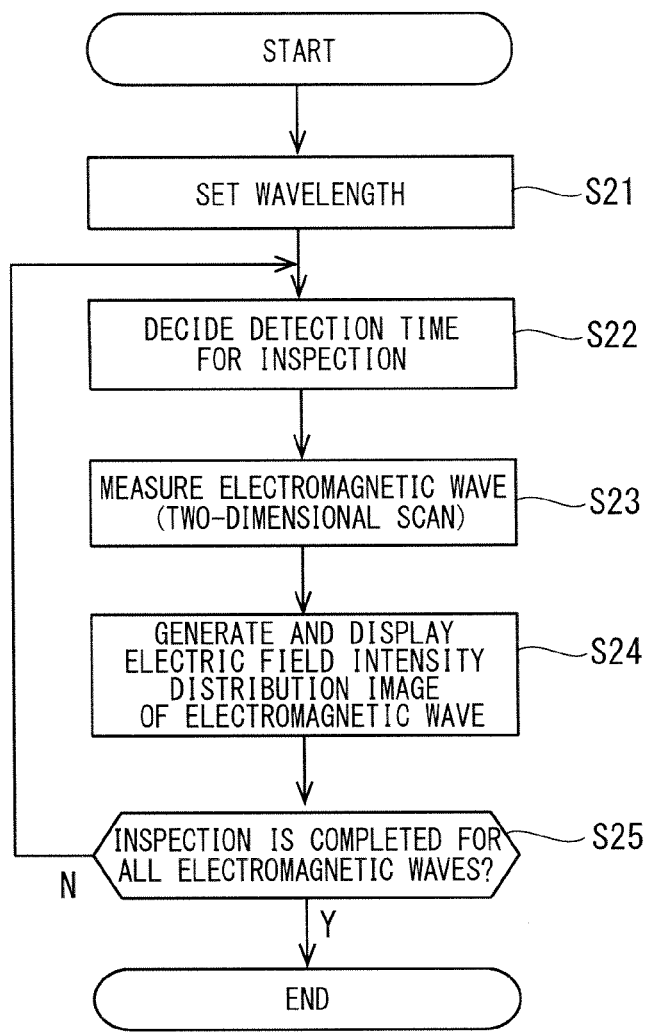
FIG. 9 is a view illustrating a flow of an inspection example 2.

FIG. 9 is a view illustrating a flow of an inspection example 2. In the inspection example 2, the electromagnetic wave emitted from a whole or a partial area of the multi-junction type solar cell 90 is measured to form the electric field intensity distribution image of the electromagnetic wave. In the inspection example 2, because a certain amount of wide range can be inspected, the characteristics of the portions can be compared to each other, and a defective place can be easily detected.

Specifically, the wavelength of the pulse light used in the irradiation is set based on the absorption wavelength region of each layer of the multi-junction type solar cell 90 (Step S21). Step S21 is similar to Step S11 shown in FIG. 5. At this point, it is assumed that the pieces of pulse light LP11, LP21, and LP31 having three wavelengths $\lambda$, $\lambda/2$, and $\lambda/3$ are set such that the multi-junction type solar cell 90 is irradiated with the pieces of pulse light LP11, LP21, and LP31.

Then a detection time for inspection is decided (Step S22). Specifically, the multi-junction type solar cell 90 is irradiated with the pulse light having a specific wavelength in the plural wavelengths set in Step S21 (in this case, the pulse light LP11 is decided to be the pulse light having the specific wavelength), and the time waveform of the electromagnetic wave LT11 emitted from the multi-junction type solar cell 90 is restored. The time (that is, the position of the delay stage of the delay element 14) the electric field intensity is maximized in the time waveform is set to the detection time for inspection.

The inspection object range of the multi-junction type solar cell 90 is irradiated with the pulse light LP11 to measure the emitted electromagnetic wave LT11 (Step S23). Specifically, the delay stage of the delay element 14 is fixed to the position corresponding to the detection time for inspection decided in Step S22. At this point, the inspection object range of the multi-junction type solar cell 90 is two-dimensionally scanned with the pulse light LP11.

The detection time for inspection decided in Step S22 is not necessarily the detection time the maximum electric field intensity is detected. However, in Step S23, the electromagnetic wave emitted from each portion of the multi-junction type solar cell 90 is easily detected by fixing the detection time for inspection to the detection time the maximum electric field intensity is detected.

When the measurement of the electromagnetic wave LT11 is completed in Step S23, the electric field intensity distribution image is generated by the image generation part 21, and displayed on the monitor 17 (Step S24).

Next, whether the measurement is completed for all the electromagnetic waves is determined (Step S25). When it is determined that the measurement is completed, the inspection is ended. On the other hand, when it is determined that the measurement is not completed, the flow returns to Step S22. At this point, because the inspection object range is not irradiated with other pieces of pulse light LP21 and LP31, the flow returns to Step S22. Then, the inspection object range is irradiated with the pulse light LP21 to measure the electromagnetic wave LT21, and the inspection object range is irradiated with the pulse light LP31 to measure the electromagnetic wave LT31. In Step S24, the electric field intensity distribution images of the electromagnetic waves LT21 and LT31 are generated and displayed.

Alternatively, Step S24 (that is, the step of generating and displaying the electric field intensity distribution image) may be performed after it is determined that the measurement is completed for all the electromagnetic waves in Step S25.

Figure 10:
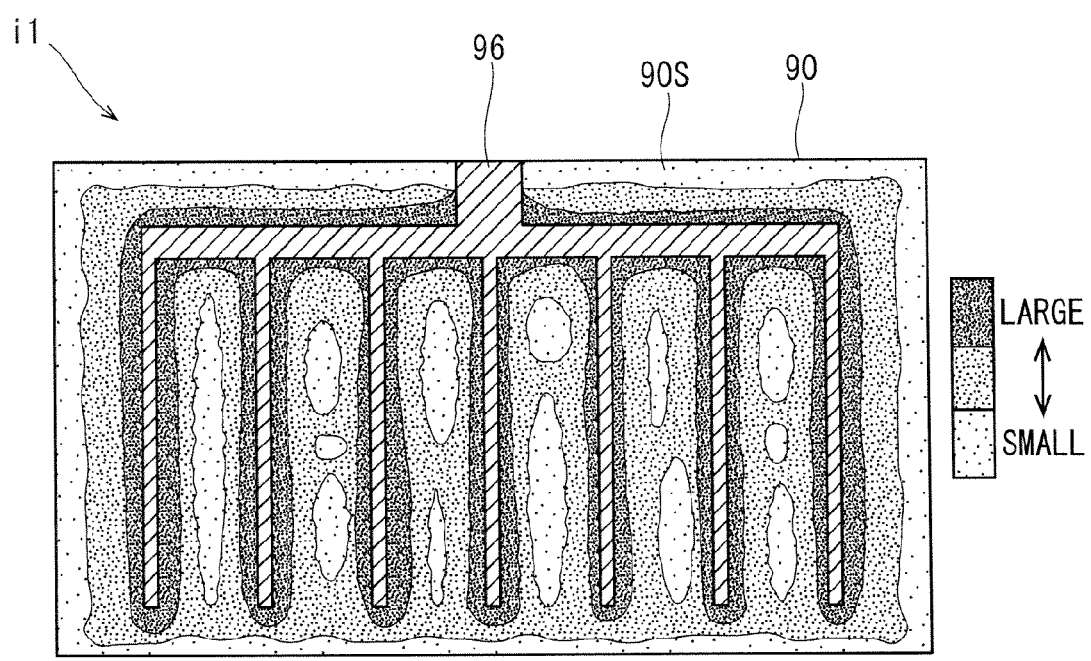
FIG. 10 is a schematic diagram illustrating an example of an electric field intensity distribution image.

FIG. 10 is a schematic diagram illustrating an example of an electric field intensity distribution image i1. According to the electric field intensity distribution image i1, the electric field intensity distribution in the multi-junction type solar cell 90 can easily be understood. For example, the defective place of the multi unction type solar cell 90 can easily be identified based on the electric field intensity distribution.

For example, the plural electric field intensity distribution images obtained in Step S25 are synthesized into one image, and the image may be displayed on the monitor 17. For example, for the three electric field intensity distribution images, the electric field intensity distribution images may be colored in red (R), green (G), and blue (B), respectively, and synthesized into one image. Therefore, the three electric field intensity distributions can individually be understood in one synthetic image.

1.3 Advantageous Effect

According to the first preferred embodiment, in the multi-junction type solar cell 90 having the different absorption wavelength regions in the depth direction, the solar cell layer existing at the position of the target depth is irradiated with the light having the wavelength corresponding to the solar cell layer, and the electromagnetic wave emitted from the position of the target depth can be measured. Therefore, each portion of the multi-junction type solar cell 90 can well be inspected in the depth direction.

There is a well known quantum-dot solar cell in which quantum dots are stacked from the back side to the light receiving surface side such that a dot size decreases gradually. In the quantum-dot solar cell, because the dot size varies, the absorption wavelength varies in the depth direction. The inspection apparatus 100 is useful for inspecting the quantum-dot solar cell because the inspection is performed using the plural pieces of pulse light having the different wavelengths.

Generally, it is well known that long-wavelength light invades to a deeper portion while short-wavelength light invades only to a shallower portion. That is, each portion of the solar cell can well be inspected in the depth direction by irradiating the single-junction solar cell with the plural pieces of pulse light having different wavelengths.

In a field of the image sensor, there is well known an image sensor, such as Foveon X3 (registered trademark), in which plural silicon layers having different absorption wavelength regions are stacked. In the case that such image sensors are inspected, each layer can be inspected by irradiating the layer with the pulse light having the wavelength corresponding to the layer.

For the inspection of the LED, when the LED is irradiated with the light having the wavelength shorter than an oscillation wavelength of a certain semiconductor layer, the light is absorbed to be able to emit the electromagnetic wave. Accordingly, the LED can well be inspected when irradiated with the light having the wavelength shorter than the oscillation wavelength (that is, the light having the energy higher than the energy gap).

The wavelength of the pulse light with which the photo device is irradiated may be decided as follows. For example, it is assumed that the photo device of the inspection target includes a first layer, and a second layer which is provided below the first layer, the second layer having the absorption wavelength region different from that of the first layer. In this case, the photo device may be irradiated with first light having the energy higher than the energy gap of the first layer and second light having the energy that is higher than the energy gap of the second layer and is lower than the energy gap of the first layer. In this case, the electromagnetic wave can selectively be emitted from the first layer by irradiating the photo device with first light, and the electromagnetic wave can selectively be emitted from the second layer by irradiating the photo device with second light.

2. Second Preferred Embodiment

Figure 11:
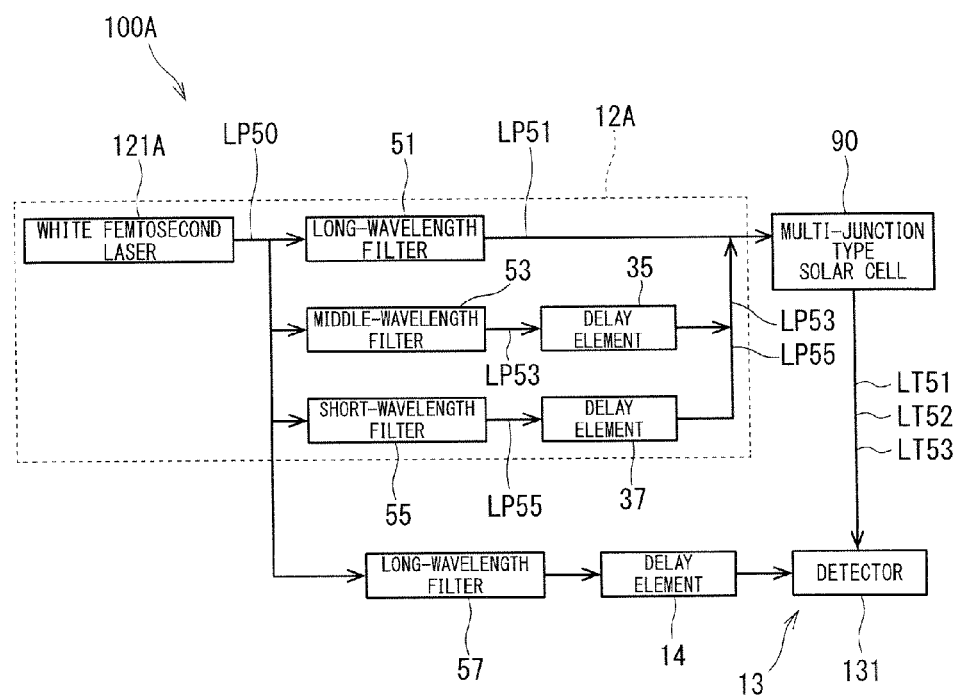
FIG. 11 is a schematic diagram illustrating a configuration of an inspection apparatus according to a second preferred embodiment.

FIG. 11 is a schematic diagram illustrating a configuration of an inspection apparatus 100A according to a second preferred embodiment. In the following description, the component having a function similar to that of the first preferred embodiment is designated by the identical numeral, and sometimes the description is omitted.

The inspection apparatus 100A includes a white femtosecond laser 121A as a light source of an irradiation part 12A. White pulse light LP50 emitted from the white femtosecond laser 121A is split, and passes through a long-wavelength filter 51, a middle-wavelength filter 53, and a short-wavelength filter 55. Therefore, plural pieces of pulse light LP51, LP53, and LP55 having wavelengths different from one another, and the multi-junction type solar cell 90 is irradiated with the pieces of pulse light LP51, LP53, and LP55. In the second preferred embodiment, the multi-junction type solar cell 90 can be irradiated with the pieces of pulse light LP51, LP53, and LP55 while the delay elements 35 and 37 temporally shift the pieces of pulse light LP51, LP53, and LP55 from one another. The electromagnetic waves LT51, LT52, and LT53 are emitted from the multi-junction type solar cell 90 by irradiating the multi-junction type solar cell 90 with the pieces of pulse light LP51, LP53, and LP55, respectively.

In the second preferred embodiment, the white pulse light LP50 is incident to the detector 131 after passing through a long-wavelength filter 57. Therefore, the detector 131 detects the electromagnetic wave emitted from the multi-junction type solar cell 90. It is not always necessary to use the long-wavelength filter 57, but a wavelength filter may properly be selected according to a material of the detector 131. The optical path length of the pulse light incident to the detector 131 can be changed by the delay element 14. Therefore, the time the detector 131 detects the electromagnetic wave can be changed.

In the inspection apparatus 100A, similarly to the inspection apparatus 100, the multi-junction type solar cell 90 can well be inspected.

3. Third Preferred Embodiment

Figure 12:
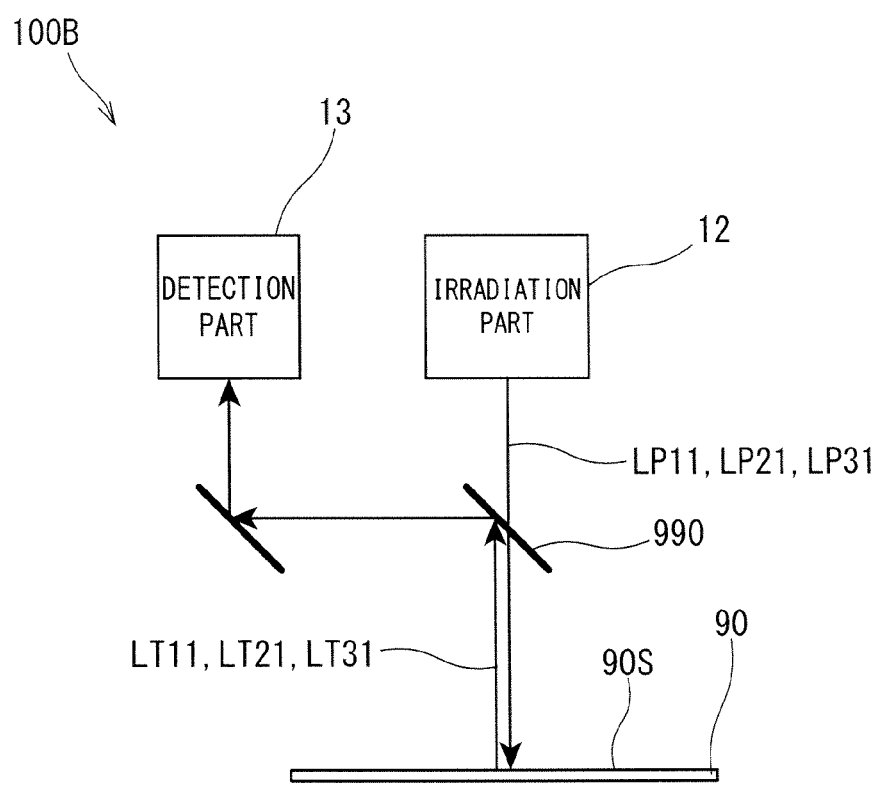
FIG. 12 is a schematic diagram illustrating an inspection apparatus according to a third preferred embodiment.

FIG. 12 is a schematic diagram illustrating an inspection apparatus 100B according to a third preferred embodiment. In the inspection apparatus 100B, the pulse light emitted from the irradiation part 12 is transmitted through a transparent conductive substrate (ITO) 990, and is perpendicularly incident to the surface 90S of the multi-junction type solar cell 90. In the electromagnetic wave generated in response to the irradiation of the multi-junction type solar cell 90 with the pulse light, the electromagnetic wave emitted onto the side of the surface 90S is reflected by the transparent conductive substrate 990, and is incident to the detector 131 through an optical system such as a lens. That is, the inspection apparatus 100B is configured as a coaxial reflection type apparatus in which the pulse light used in the irradiation is coaxial with the emitted electromagnetic wave. In the inspection apparatus 100B, similarly to the inspection apparatus 100, the electromagnetic wave emitted from the multi-junction type solar cell 90 can be detected.

4. Fourth Preferred Embodiment

FIG. 13 is a schematic diagram illustrating an inspection apparatus 100C according to a fourth preferred embodiment. In the inspection apparatus 100C, the pulse light emitted from the irradiation part 12 is perpendicularly incident to the surface 90S of the multi-junction type solar cell 90. The detection part 13 detects the electromagnetic wave emitted (that is, transmitted) onto the hack side of the multi-junction type solar cell 90. That is, the inspection apparatus 100C is configured as a transmission type inspection apparatus. In the inspection apparatus 100C, similarly to the inspection apparatus 100, the electromagnetic wave emitted from the multi-junction type solar cell 90 can be detected.

<Modifications>

The preferred embodiments are described above. The present invention is not limited to the above embodiment, but various modifications can be made in the present invention.

For example, in the first preferred embodiment, the femtosecond laser 121 emits the pulse light, and the multi-junction type solar cell 90 emits the pulse-shape electromagnetic wave. Alternatively, two light sources that emit two pieces of continuous light having oscillation frequencies slightly different from each other can be used instead of the femtosecond laser 121. Specifically, the two pieces of continuous light are overlapped with each other using a coupler formed by an optical fiber that is of an optical waveguide, thereby generating an optical beat signal corresponding to a difference between the frequencies. The electromagnetic wave (terahertz wave) corresponding to the frequency of the optical beat signal can be emitted by irradiating the multi-junction type solar cell 90 with the optical beat signal. A distributed-feedback (DFB) laser that substantially continuously (for example, every 2 nm) changes the wavelength of an emitted laser beam by temperature control can be used as the light source.

In this case, for example, six light sources may be used when the multi-junction type solar cell 90 is irradiated with three pieces of light (optical beat signals) having different wavelengths. Desirably the multi-junction type solar cell 90 is irradiated with the plural optical heat signals having different wavelengths while the optical heat signals are switched. Alternatively, the multi-junction type solar cell 90 may simultaneously be irradiated with the optical beat signals. This is because the electromagnetic wave emitted by irradiating the multi-junction type solar cell 90 with the optical beat signal has an extremely narrow frequency distribution. For this reason, electromagnetic wave components can easily be separated from one another using a frequency-dependent filter.

While the invention has been shown and described in detail, the foregoing description is in all aspects illustrative and not restrictive. It is therefore understood that numerous modifications and variations can be devised without departing from the scope of the invention.

What is claimed is:

1. An inspection apparatus that inspects a photo device, the inspection apparatus comprising:
   an irradiation part that emits a plurality of pieces of pulse light having different wavelengths to irradiate a photo device;
   a setting part that sets said wavelengths of said plurality of pieces of pulse light with which said photo device is irradiated by said irradiation part; and
   a detection part that detects an electric field intensity of an electromagnetic wave emitted from said photo device in response to said plurality of pieces of pulse light with which said photo device is irradiated by said irradiation part, wherein
   said irradiation part irradiates said photo device with pulse light having a second wavelength different from a first wavelength after a time $\Delta t$ elapses since said photo device is irradiated with pulse light having said first wavelength, and
   said time $\Delta t$ is longer than a generation time for one pulse of said electromagnetic wave emitted by said pulse light.

2. The inspection apparatus according to claim 1, further comprising a delay part that delays a time a detector detects said electromagnetic wave relative to a time said detector receives said pulse light,
   said detection part includes said detector that detects said electromagnetic wave by receiving said pulse light emitted from said irradiation part.

3. The inspection apparatus according to claim 1, further comprising:
   a scanning mechanism that scans said photo device with said plurality of pieces of pulse light with which said photo device is irradiated by said irradiation part; and
   an image generation part that generates an image indicating an electric field intensity distribution in said photo device based on said electric field intensity of said electromagnetic wave detected by said detection part.

4. The inspection apparatus according to claim 1, wherein said photo device is constructed by stacking materials having different absorption wavelength regions.

5. The inspection apparatus according to claim 4, wherein said photo device includes a first layer, and a second layer having an absorption wavelength region different from that of said first layer, said second layer being provided below said first layer, and
   said plurality of pieces of pulse light having said different wavelengths includes first light having energy higher than an energy gap of said first layer and second light having energy that is higher than an energy gap of said second layer and is lower than said energy gap of said first layer.

6. The inspection apparatus according to claim 4, wherein said photo device is a multi junction type solar cell.

7. An inspection method for inspecting a photo device, the inspection method comprising the steps of:
- emitting a plurality of pieces of pulse light having different wavelengths to irradiate a photo device;
- setting said wavelengths of said plurality of pieces of pulse light with which said photo device is irradiated in said irradiation step; and
- detecting an electromagnetic wave emitted from said photo device in response to said plurality of pieces of pulse light with which said photo device is irradiated in said irradiation step,
- wherein said irradiation step includes the step of irradiating said photo device with pulse light having a second wavelength different from a first wavelength after a time $\Delta t$ elapses since said photo device is irradiated with pulse light having said first wavelength, and
- said time $\Delta t$ is longer than a generation time for one pulse of said electromagnetic wave emitted by said pulse light.

* * * * *